US008710181B2

(12) United States Patent
Christiansen et al.

(10) Patent No.: US 8,710,181 B2
(45) Date of Patent: Apr. 29, 2014

(54) USE OF TRIS(HYDROXYMETHYL) AMINOMETHANE FOR THE STABILIZATION OF PEPTIDES, POLYPEPTIDES AND PROTEINS

(75) Inventors: Ingun Christiansen, Birkerod (DK); Arne Staby, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 762 days.

(21) Appl. No.: 11/661,521

(22) PCT Filed: Aug. 26, 2005

(86) PCT No.: PCT/EP2005/054209
§ 371 (c)(1),
(2), (4) Date: Sep. 28, 2007

(87) PCT Pub. No.: WO2006/024631
PCT Pub. Date: Mar. 9, 2006

(65) Prior Publication Data
US 2008/0171848 A1 Jul. 17, 2008

Related U.S. Application Data

(60) Provisional application No. 60/606,788, filed on Sep. 1, 2004.

(30) Foreign Application Priority Data

Aug. 31, 2004 (DK) .......................... PA 2004 01310

(51) Int. Cl.
| *A61K 38/28* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 2/00* | (2006.01) |
| *C07K 4/00* | (2006.01) |
| *A61K 38/26* | (2006.01) |
| *C07K 1/00* | (2006.01) |
| *C07K 1/113* | (2006.01) |

(52) U.S. Cl.
CPC ...................................... *C07K 1/113* (2013.01)
USPC ............ 530/303; 530/300; 530/308; 530/344

(58) Field of Classification Search
None
See application file for complete search history.

(56) References Cited

U.S. PATENT DOCUMENTS

| 4,468,346 | A | * | 8/1984 | Paul et al. ................. 530/388.25 |
| 5,206,219 | A | | 4/1993 | Desai |
| 5,272,135 | A | | 12/1993 | Takruri |
| 5,455,331 | A | | 10/1995 | Pearce |
| 5,652,216 | A | | 7/1997 | Kornfelt et al. |
| 5,705,483 | A | | 1/1998 | Galloway et al. |
| 6,133,229 | A | * | 10/2000 | Gibson et al. ...................... 514/2 |
| 6,184,201 | B1 | | 2/2001 | Drucker et al. |
| 6,268,343 | B1 | | 7/2001 | Knudsen et al. |
| 6,274,553 | B1 | | 8/2001 | Furuya et al. |
| 6,284,727 | B1 | * | 9/2001 | Kim et al. ......................... 514/12 |
| 6,380,357 | B2 | | 4/2002 | Hermeling et al. |
| 6,384,016 | B1 | | 5/2002 | Kaarsholm |
| 6,444,788 | B1 | * | 9/2002 | Staby ............................ 530/344 |
| 6,586,399 | B1 | | 7/2003 | Drucker et al. |
| 6,844,321 | B2 | | 1/2005 | Arentsen |
| 7,022,674 | B2 | | 4/2006 | DeFelippis et al. |
| 7,049,284 | B2 | | 5/2006 | Drucker et al. |
| 7,056,886 | B2 | | 6/2006 | Isaacs |
| 7,112,567 | B2 | | 9/2006 | Bridon et al. |
| 7,238,663 | B2 | | 7/2007 | DeFelippis et al. |
| 8,114,959 | B2 | * | 2/2012 | Juul-Mortensen ............ 530/308 |
| 2001/0014666 | A1 | | 8/2001 | Hermeling et al. |
| 2001/0027180 | A1 | | 10/2001 | Isaacs |
| 2002/0151467 | A1 | | 10/2002 | Leung |
| 2003/0027996 | A1 | * | 2/2003 | Staby ............................ 530/416 |
| 2003/0060412 | A1 | | 3/2003 | Prouty, Jr. et al. |
| 2003/0069182 | A1 | | 4/2003 | Rinella, Jr. |
| 2003/0119734 | A1 | | 6/2003 | Flink et al. |
| 2003/0158101 | A1 | | 8/2003 | Drucker |
| 2003/0207802 | A1 | | 11/2003 | DeFelippis et al. |
| 2003/0220243 | A1 | | 11/2003 | Glaesner et al. |
| 2003/0220255 | A1 | | 11/2003 | Knudsen et al. |
| 2004/0248782 | A1 | | 12/2004 | Bridon et al. |
| 2006/0084605 | A1 | | 4/2006 | Engelund et al. |

(Continued)

FOREIGN PATENT DOCUMENTS

| EP | 0431679 | 11/1990 |
| EP | 0438767 | 12/1990 |

(Continued)

OTHER PUBLICATIONS

Senderoff, R.I. et al, Consideration of Conformational Transitions and Racemization during Process Development of Recombinant Glucagon-like Peptide-1, Journal of Pharmaceutical Sciences, 1998, 183-189, vol. 87—No. 2, American Chemical Society & American Pharm. Assc.

(Continued)

*Primary Examiner* — Marcela M Cordero Garcia
(74) *Attorney, Agent, or Firm* — Rosemarie R. Wilk-Orescan

(57) ABSTRACT

The present invention is directed to a method for reducing the onset or incidence of gelation/fibrillation/aggregation during the up- and down-stream processing and purification of peptides, polypeptides and proteins analogs and/or derivatives thereof, including Glucagon-Like Peptides (GLPs). More particularly, the present invention relates to methods of processing and purifying such peptides, polypeptides and proteins in the presence of tris(hydroxymethyl)aminomethane.

18 Claims, 1 Drawing Sheet

(56) References Cited

U.S. PATENT DOCUMENTS

| | | | |
|---|---|---|---|
| 2006/0183682 A1* | 8/2006 | Juul-Mortensen | 514/12 |
| 2006/0287221 A1 | 12/2006 | Knudsen et al. | |
| 2008/0318865 A1* | 12/2008 | Juul-Mortensen | 514/12 |

FOREIGN PATENT DOCUMENTS

| | | | |
|---|---|---|---|
| EP | 699687 | 8/1995 | |
| EP | 0708179 | 4/1996 | |
| EP | 747390 | 12/1996 | |
| EP | 0926159 | 6/1999 | |
| EP | 1329462 | 10/2001 | |
| EP | 1424077 | 5/2002 | |
| EP | 1344533 | 9/2003 | |
| EP | 1396499 | 3/2004 | |
| JP | 10101696 | 4/1998 | |
| JP | 2001-525371 | 12/2001 | |
| JP | 2002-508332 | 3/2002 | |
| JP | 2002532557 | 10/2002 | |
| PA | 200101010 | 6/2001 | |
| RU | 2180218 | 3/2002 | |
| WO | WO9000200 | 1/1990 | |
| WO | WO9219260 | 11/1992 | |
| WO | WO9323010 | 11/1993 | |
| WO | WO9522560 | 2/1995 | |
| WO | 95/10605 | 4/1995 | |
| WO | WO9513825 | 5/1995 | |
| WO | WO9620005 | 7/1996 | |
| WO | WO9638469 | 12/1996 | |
| WO | WO9808871 | 3/1998 | |
| WO | WO9831386 | 7/1998 | |
| WO | WO9916417 | 4/1999 | |
| WO | WO 99/21889 | * 5/1999 | C07K 14/65 |
| WO | WO9929336 | 6/1999 | |
| WO | WO9930731 | 6/1999 | |
| WO | WO9943341 | 9/1999 | |
| WO | WO9943706 | 9/1999 | |
| WO | WO9943707 | 9/1999 | |
| WO | WO0149314 | 12/1999 | |
| WO | WO0015224 | 3/2000 | |
| WO | WO 00/37098 | 6/2000 | |
| WO | WO0041546 | 7/2000 | |
| WO | WO0055119 | 9/2000 | |
| WO | WO0100223 | 1/2001 | |
| WO | WO0143762 | 6/2001 | |
| WO | 01/52937 | 7/2001 | |
| WO | WO 01/49314 | 7/2001 | |
| WO | WO0155213 | 8/2001 | |
| WO | WO0177141 | 10/2001 | |
| WO | WO0267989 | 1/2002 | |
| WO | WO0247715 | 6/2002 | |
| WO | WO0248183 | 6/2002 | |
| WO | WO03002136 | 1/2003 | |
| WO | WO03013589 | 2/2003 | |
| WO | WO03020201 | 3/2003 | |
| WO | WO03035099 | 5/2003 | |
| WO | WO2004029076 | 4/2004 | |
| WO | WO2004105781 | 12/2004 | |
| WO | WO2005000222 | 1/2005 | |
| WO | WO2005/046716 | 5/2005 | |
| WO | WO2006025882 | 3/2006 | |

OTHER PUBLICATIONS

S.E. Bondos & A. Bicknell, Detection and prevention of protein aggregation before during and after purification, Analytical Biochemistry, 2003, 223-231, vol. 316, Academic Press.

Blundell, T.L., Springer Verlag, 1983, pp. 37-55.

Non-final Office Action dated Dec. 9, 2009 in U.S. Appl. No. 12/184,531, filed Aug. 1, 2008 by Juul-Mortensen.

Bailey et al. The Kinetics of Enzyme-Catalysed Reactions Biochemical Engineering Fundamentals, $2^{nd}$ Ed., pp. 129-148 (1986).

Chou, J. Z. et al., Journal of Pharmaceutical Sciences, A Radioimmunoassay for LY315902, An Analog of Glucagon-Like Insulinotropic Pepride, and Its Application in the Study of Canine Pharmacokinetics, vol. 86(7), pp. 768-773 (1997).

D. Voet and J.G. Voet, Biochem, $2^{nd}$ Ed., pp. 235-241 (1995).

D.E. Smilek et al., Proc Natl Acad Sci USA, vol. 88, pp. 9633-9637, (1991).

Entry for Glycerin in Drugs.Com (www.drugs.com/ppa/glycerin-glycerol.html), Printed Aug. 4, 2009.

European Pharmacopoeia, 2007, vol. 1, p. 730, Council of Europe-Strasbourg.

G.F. Stamper et al., "Accelerated Stability Testing of Proteins and Peptides: PH-Stability Profile of Insulinotropin Using Traditional Arrheneius and Non-Linear Fitting Analysis", Drug Development and Industrial Pharmacy, 1995, vol. 21, No. 13, pp. 1503-1511.

H. Qi et al., "Stability and Stabilization of Insulinotropin in a Dextran Formulation", PDA Journal of Pharmaceutical Science & Technology, vol. 49, No. 6, Nov.-Dec. 1995, pp. 289-293.

H.J.C. Berendsen, A Glimpse of the Holy Grail, Science, vol. 282, pp. 642-643 (1998).

http://www.copewithcytokines.de/cope.cgi?key=insulinotropin; (Host Ibelgauft's Cope: Cytokines & Cells Online Pathfinder Encyclopedia; Insulinotropin).

http://www.copewithcytokineslde/cope.cgi?key=glp%2dl; (Host Ibelgauft's Cope: Cytokines & Cells Online Pathfinder Encyclopedia; GLP-1).

http://www.fermantas.com/techinfo/appendix/appendixtables1.htm, 'Temperature Dependence of the PH for Commonly Used Buffers' + 'Temperature Dependence of the PH of 50 MM Tris-HCL Solutions'.

Larsen, P.J. et al., Systemic Administration of the LOGN Acting GLP-1, Diabetes, vol. 50, 2530-9, 2000.

Malendowicz, L.K. et al., "Preproglucagon Derived Peptides and Thyrotropin (TSH) Secretion in the Rat: Robust and Sustained Lowering of Blood TSH Levels in Extendin-4 Injected Animals", International Journal of Molecular Medicine, vol. 10, pp. 327-331 (2002).

N. Good et al., "Hydrogen Ion Buffers for Biological Research", Biochemistry, 1966, vol. 5, No. 2, pp. 467-477.

Rudinger, In: Peptide Hormones, Ja Parsons, Ed., pp. 1-7 (1976).

Shinotesuto, Patentabstracts of Japan, of JP10101696.

Sigma, http://www.sigma-genosys.com/peptide design.asp (Accessed Dec. 16, 2004).

Singh, S. et al. AAPS Pharmscitech, vol. 4(3), pp. 334-342 (2003).

Skovgaard et al., "Using Evolutionary Information and Ancestral Sequences to Understand the Sequence-Function Relationship in GLP-1 Agonists," J. Mol. Bio., 2006, vol. 363, pp. 977-988.

Tsoka et al, Selective Flocculation Ands Precipitation for the Improvement of Virus-Like Particle Recovery From Yeast Homogenate, Biotechnol Prog. vol. 16(4), pp. 661-667 (2000).

W.S. Messer, Vasopressin and Oxytocin, http://www.neurosci.pharm.utoldeo.edu/mbc3320/vasopressin.htm.

Non-Final Office Action in U.S. Appl. No. 11/290,635, filed Nov. 30, 2005, Inventors: Juul-Mortensen et al. Sent Feb. 2, 2007.

Final Office Action in U.S. Appl. No. 11/290,635, filed Nov. 30, 2005, Inventors: Juul-Mortensen Sent Sep. 5, 2007.

Brittain, Harry G., Buffers, Buffering Agents, and Ionic Equilibria, Encyclopedia of Pharmaceutical Technology, p. 385, 2007.

* cited by examiner

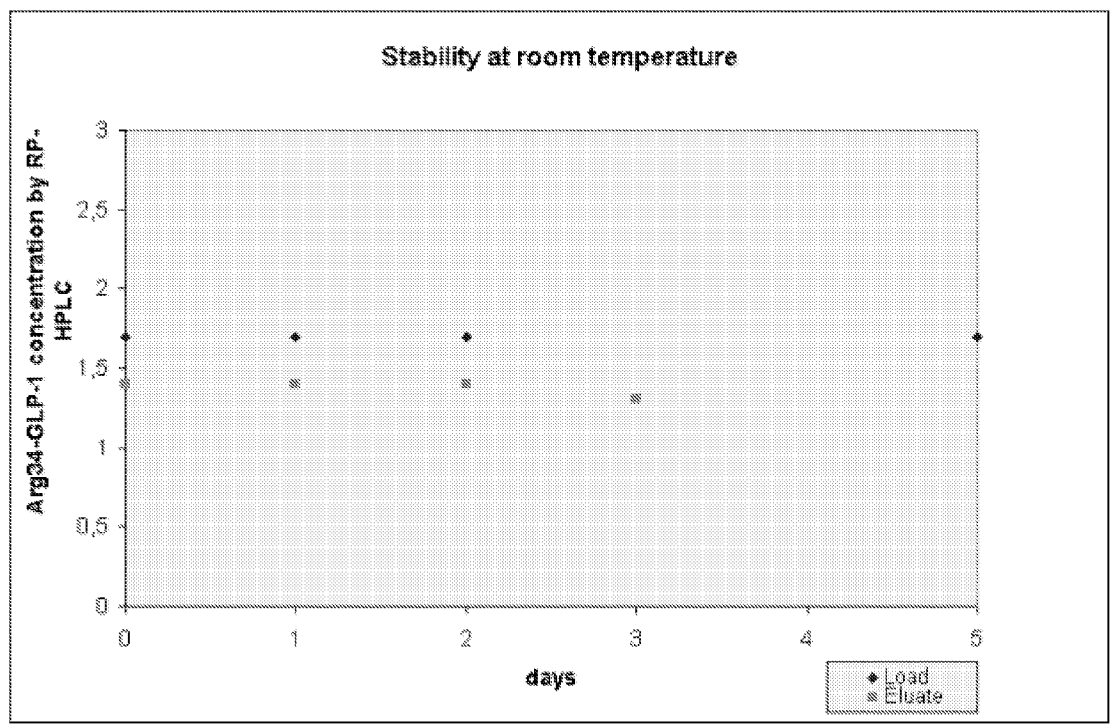

1

USE OF TRIS(HYDROXYMETHYL) AMINOMETHANE FOR THE STABILIZATION OF PEPTIDES, POLYPEPTIDES AND PROTEINS

CROSS-REFERENCE TO RELATED APPLICATIONS

This application is a 35 U.S.C. §371 National Stage application of International Patent Application PCT/EP2005/054209 (published as WO 2006/024631), filed Aug. 26, 2005, which claimed priority of Danish Patent Application PA 2004 01310, filed Aug. 31, 2004; this application further claims priority under 35 U.S.C. §119 of U.S. Provisional Application 60/606,788, filed Sep. 1, 2004.

FIELD OF THE INVENTION

This invention relates generally to a method for reducing the onset or incidence of gelation/fibrillation/aggregation during the up- and down-stream processing and purification of peptides, polypeptides and proteins.

BACKGROUND OF THE INVENTION

A large number of polypeptides have been approved for use in medical practice. These polypeptides may be produced in suitable host cells by recombinant DNA technology or they may be produced synthetically by well established peptide synthesis technology. However, native polypeptides as well as analogues and derivatives thereof tend to exhibit high clearance rates which are unacceptable for many clinical indications where a high plasma concentration of the peptide is required over a prolonged period of time. Examples of peptides that in their native form having a high clearance rate are: ACTH, corticotropin-releasing factor, angiotensin, calcitonin, exendin, exendin-3, exendin-4, insulin, glucagon, glucagon-like peptide-1, glucagon-like peptide-2, insulin-like growth factor-1, insulin-like growth factor-2, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opioids and analogues thereof, superoxide dismutase, interferon, asparaginase, arginase, arginine deaminase, adenosine deaminase and ribonuclease.

While a number of aqueous formulations which stabilize peptide, polypeptide and protein compositions have been identified in the art, the destabilization of peptides, polypeptides and proteins in both formulation solutions and in solution during processing continues to create difficulty, especially in the up- and down-stream processing of these peptides. Consequently, there is a need for new methods which overcome the insufficiencies of the prior art. (Senderhoff et al., J. Pharm. Sc. Vol. 87, No. 2, pp. 183-189, February 1998).

EP 1 396 499 describes a process for stabilizing glucagon-like peptide (GLP-1) compounds.

EP 0 747 390 describes methods of reducing gelation of a fatty acid acylated protein using a citrate buffer.

S. E. Bondos and A. Bicknell Analytical Biochemistry 316 (2003)223-231. Tris(hydroxymethyl)aminomethane is not mentioned as an agent that may promote protein solubility in this article.

SUMMARY OF THE INVENTION

The present invention is directed to methods for reducing the onset or incidence of gelation/fibrillation/aggregation during the up- and down-stream processing and purification of peptides, polypeptides and proteins including Glucagon-Like Peptides (GLPs), exendin and analogs and/or derivatives thereof.

The present invention provides a method for processing an aqueous solution of peptides, polypeptides and proteins with or without an organic modifier at higher concentrations, with less temperature control and pH control than currently practiced methods.

More particularly, the present invention relates to a method of processing and purifying peptides, polypeptides and proteins including Glucagon-Like Peptide (GLP) compounds in the presence of tris(hydroxymethyl)-aminomethane (TRIS).

The present invention also provides aqueous solutions of peptides, polypeptides and proteins having a reduced tendency to gel/fibrillate/aggregate.

BRIEF DESCRIPTION OF THE DRAWING

FIG. 1: A graphical representation of a stability study for an aqueous solution of $Arg^{34}$-GLP-1[7-37] containing approximately 2% by weight ethanol and 10 mM of tris-(hydroxymethyl)aminomethane, at pH 9.2, room temperature.

DETAILED DESCRIPTION OF THE INVENTION

The present invention details the surprising discovery that by processing peptides or proteins in the presence of a TRIS buffering agent or TRIS additive, such as in the process stream, particularly a process stream containing a polar organic solvent such as ethanol, the tendency of peptides, polypeptides and proteins to form a gel, fibrillate or aggregate is greatly reduced.

In methods of the present invention, tris-(hydroxymethyl) aminomethane, and similar biological buffering substances have shown to be superior in stabilizing peptides, polypeptides and proteins, including Glucagon-Like Peptides (GLPs, analogs and derivatives thereof) in solution, during up- and down-stream processing and in preventing the physical degradation of the final drug product. TRIS generally refers to 2-amino-2-hydroxymethyl-1,3-propanediol, and to any pharmaceutically acceptable salt thereof. The free base and the hydrochloride form are two common forms of TRIS. TRIS is also known in the art as trimethylol aminomethane, tris amine buffer, THAM, and tromethamine. TRIS has a $pK_A$ of about 8.05. TRIS used as an "additive" refers to the use of TRIS outside of its typical buffering range, for example below a pH of about 7.0, or above a pH of about 9.1.

Up- or down-stream processing and purification of peptides, polypeptides and proteins includes, but is not limited to fermentation, rotary evaporation, cultivation, filtration, centrifugation, chromatography methods, enzymatic synthesis, organic synthesis, enzymatic conversion, precipitation, crystallization, lyophilization, freeze drying or other means known to the skilled artesian.

The term "organic modifiers" refers to an organic solvent or organic compound soluble in water or mixtures thereof, which modifier induces a favorable and changed selectivity between the unwanted related impurity or impurities and the peptide and the ion exchanger. Whether or not a selected modifier induces said selectivity will usually depend on the related impurity or impurities, and may be tested by trial-and-error. The organic modifier includes but is not limited to $C_{1-6}$-alkanol, $C_{1-6}$-alkenol or $C_{1-6}$-alkynol, acetonitrile, N-methylpyrrolidone, urea, guanidine-HCl, or $C_{1-6}$-alkanoic acid, such as acetic acid, $C_{2-6}$-glycol, $C_{3-7}$-polyalcohol including sugars or mixtures thereof.

The term "$C_{1-6}$-alkanol", "$C_{1-6}$-alkenol" or "$C_{1-6}$-alkynol", as used herein, alone or in combination is intended to include those $C_{1-6}$-alkane, $C_{1-6}$-alkene or $C_{1-6}$-alkyne groups of the designated length in either a linear or branched or cyclic configuration whereto is linked a hydroxyl (—OH) (cf. Morrison & Boyd, Organic Chemistry, $4^{th}$ ed.). Examples of linear alcohols are methanol, ethanol, n-propanol, allyl alcohol, n-butanol, n-pentanol and n-hexanol. Examples of branched alcohols are 2-propanol and tert-butyl alcohol. Examples of cyclic alcohols are cyclopropyl alcohol and 2-cyclohexen-1-ol.

The term "$C_{1-6}$-alkanoic acid", as used herein, is intended to include a group of the formula R'COOH wherein R' is H or $C_{1-5}$-alkyl, such as acetic, propionic, butyric, α-methylbutyric, or valeric acid (cf. Morrison & Boyd, Organic Chemistry, $4^{th}$ ed.).

The term "$C_{1-5}$-alkyl", as used herein, is intended to include a branched or straight alkyl group having from one to five carbon atoms. Typical $C_{1-5}$-alkyl groups include, but are not limited to methyl, ethyl, n-propyl, isopropyl, butyl, isobutyl, sec-butyl, tert-butyl, pentyl, isopentyl, and the like (cf. Morrison & Boyd, Organic Chemistry, $4^{th}$ Ed.).

The term "$C_{2-6}$-glycol", as used herein, is intended to include a $C_{2-6}$-alkane containing two hydroxyl groups on different carbon atoms which may be adjacent or not. A typical $C_{2-6}$-glycol includes, but is not limited to 1,2-ethanediol, 1,2-propanediol, or 2-methyl-2,4-pentanediol (cf. Morrison & Boyd, Organic Chemistry, $4^{th}$ Ed.).

The term "$C_{2-6}$-alkane", as used herein, is intended to include a branched or straight alkane group having from two to six carbon atoms. Typical $C_{2-6}$-alkane groups include, but are not limited to ethane, propane, iso-propane, butane, isobutane, pentane, hexane and the like (cf. Morrison & Boyd, Organic Chemistry, $4^{th}$ Ed.).

The term "$C_{3-7}$-polyalcohol including sugars", as used herein, is intended to include a group of the formula $HOCH_2(CHOH)_nCH_2OH$ wherein n is an integer from 1-5, and monosaccharides such as mannose and glucose (cf. Morrison & Boyd, Organic Chemistry, $4^{th}$ Ed.).

The term "peptide" or "peptides", as used herein, is intended to include such polypeptides, oligopeptides, proteins, as well as homologues, analogues and derivatives thereof, which are capable of being produced by conventional recombinant DNA techniques as well as conventional synthetic methods. Such peptides include but are not limited to glucagon, hGH, insulin, aprotinin, Factor VII, TPA, Factor VIIa (NovoSeven®, available from Novo Nordisk A/S, Bagsvaerd, Denmark), Factor VIIai, FFR-Factor VIIa, heparinase, ACTH, corticotropin-releasing factor, angiotensin, calcitonin, insulin, glucagon-like peptide-1, glucagon-like peptide-2, insulin-like growth factor-1, insulin-like growth factor-2, gastric inhibitory peptide, growth hormone-releasing factor, pituitary adenylate cyclase activating peptides, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods, GIP, exendins, peptide histidine-methionine amide, helospectins, helodermin, pituitary adenylate cyclase activating peptide-related peptide, vasoactive intestinal polypeptide and analogues and derivatives thereof.

The term "GLP-1 peptide", as used herein, is intended to designate GLP-1 (7-37), GLP-1 (7-36) amide as well as analogues and derivatives thereof, which are capable of being produced by conventional recombinant DNA techniques as well as conventional synthetic methods. Such GLP-1 peptides include but are not limited to native glucagon-like peptide-1, for instance such peptide fragments which comprises GLP-1 (7-37) and functional derivatives thereof as disclosed in WO 87/06941; such peptide fragments which comprise GLP-1 (7-36) and functional derivatives thereof as disclosed in WO 90/11296; such analogues of the active GLP-1 peptides 7-34, 7-35, 7-36, and 7-37 as disclosed in WO 91/11457; such GLP-1 derivatives in which a lipophilic substituent is attached to at least one amino acid residue as disclosed in WO 98/08871; such N-terminal truncated fragments of GLP-1 as disclosed in EP 0699686-A2; and such GLP-1 analogues and derivatives that include an N-terminal imidazole group as disclosed in EP 0708179-A2.

The term "GLP-2 peptide", as used herein, is intended to designate GLP-2 (1-35), GLP-2 (1-34), GLP-2 (1-33) as well as analogues and derivatives thereof, which are capable of being produced by conventional recombinant DNA techniques as well as conventional synthetic methods. Such GLP-2 peptides include but are not limited to native glucagon-like peptide-2, GLP-2 derivatives in which a lipophilic substituent is attached to at least one amino acid residue as disclosed in WO 98/08872, human glucagon-like peptide-2 (hGLP-2), GLP-2(1-30); GLP-2(1-31); GLP-2(1-32); GLP-2(1-33); GLP-2(1-34), GLP-2(1-35), $Lys^{20}$GLP-2(1-33), $Lys^{20}Arg^{30}$GLP-2(1-33), $Arg^{30}Lys^{34}$ GLP-2(1-34), $Arg^{30}Lys^{35}$GLP-2(1-35), $Arg^{30,35}Lys^{20}$GLP-2(1-35), $Arg^{35}$GLP-2 (1-35), $Lys^{20}(N^\epsilon$-tetradecanoyl)GLP-2(1-33); $Lys^{20,30}$-bis($N^\epsilon$-tetradecanoyl)GLP-2(1-33); $Lys^{20}(N^\epsilon$-tetradecanoyl)$Arg^{30}$ GLP-2(1-33); $Arg^{30}Lys^{35}(N^\epsilon$-tetradecanoyl)GLP-2(1-35); $Arg^{30,35}Lys^{20}(N^\epsilon$-tetradecanoyl)GLP-2(1-35); $Arg^{35}Lys^{30}(N^\epsilon$-tetradecanoyl)GLP-2(1-35); $Arg^{30}Lys^{34}(N^\epsilon$-tetradecanoyl)GLP-2(1-34); $Lys^{20}(N^\epsilon$-(ω-carboxynonadecanoyl))GLP-2(1-33); $Lys^{20,30}$-bis($N^\epsilon$-(ω-carboxynonadecanoyl))GLP-2(1-33); $Lys^{20}(N^\epsilon$-(ω-carboxynonadecanoyl))$Arg^{30}$ GLP-2(1-33); $Arg^{30}Lys^{35}(N^\epsilon$-(ω-carboxynonadecanoyl))GLP-2(1-35); $Lys^{30}(N^\epsilon$-(γ-glutamyl ($N^\alpha$-tetradecanoyl)))hGLP-2, $Lys^{30}$ ($N^\epsilon$-(γ-glutamyl($N^\alpha$-hexadecanoyl)))hGLP-2, $Arg^{30,35}Lys^{20}(N^\epsilon$-(ω-carboxynonadecanoyl))GLP-2(1-35); $Arg^{35}Lys^{30}(N^\epsilon$-(ω-carboxynonadecanoyl))GLP-2(1-35); and $Arg^{30}Lys^{34}(N^\epsilon$-(ω-carboxynonadecanoyl))GLP-2(1-34).

The term "exendin" as used herein, is intended to designate exendin as well as analogs, derivatives, and fragments thereof, e.g. exendin-3 and -4. Exendin as well as analogs, derivatives, and fragments thereof are described in, for example WO 99/43708, the contents of which are herein incorporated by reference in their entirety.

The term "analogue" as used herein designates a peptide, polypeptide or protein wherein one or more amino acid residues of the parent sequence have been substituted by another amino acid residue and/or wherein one or more amino acid residues of the parent sequence have been deleted and/or wherein one or more amino acid residues have been added to the parent sequence. The term analogue also is intended to include sequences containing both peptide and non-peptide components, such as pseudopeptide or peptide mimetic residues or other non-amino acid components, as well as non-naturally occurring amino acids. Substitutions, additions or deletions can take place either at the N-terminal end or at the C-terminal end of the parent sequence or both, as well as any location within the parent sequence.

The term "derivative" as used herein designates a peptide, polypeptide or protein in which one or more of the amino acid residues of the parent sequence have been chemically modified, e.g. by alkylation, acylation, pegylation, peptide synthesis, ester formation or amide formation, or the like.

Chromatographic separation or purification of peptides, polypeptides, proteins and analogs or derivatives thereof may be performed by any method available to those skilled in the art. Examples of these techniques include, but are not limited to reverse-phase high-performance liquid chromatography (RP-HPLC), reversed-phase liquid chromatography (RP-LC), straight phase chromatography, hydrophobic interaction chromatography (HIC), hydroxyapatite chromatography, ion exchange chromatography, affinity chromatography, metal chelate chromatography, precipitation, adsorption, gel filtration, size-exclusion chromatography (SEC) electrophoresis and the like, executed singly, sequentially or as mixed-modes.

An aspect of the invention relates to a gelation fibrillation/aggregation resistant solution wherein the TRIS concentration ranges from about 1 mM to about 1000 mM, from about 1 mM to about 200 mM, from about 1 mM to about 100 mM, from about 2 mM to about 75 mM, from about 3 mM to about 50 mM, and from about 5 mM to about 25 mM.

Another aspect relates to methods of the invention wherein the pH of the solution is from about 1 to about 10, from about 2 to about 10, and from about 3 to about 9.5.

Another aspect relates to methods of the invention wherein the organic modifier is present in a concentration of from about 0% w/w to about 99% w/w, from about 0% w/w to about 70% w/w, from about 0% w/w to about 50% w/w, and from about 1% w/w to about 50% w/w.

Gelation/fibrillation/aggregation can be estimated by the Thioflavin T test (ref. ?) resulting in a colored response the degree of gelation. Another result would be increased viscosity of the gelated solution resulting in increasing back pressure on chromatographic columns during multiple runs—this is usually the first indication of gelation taking place, you will get.

Other features of the invention will become apparent in the course of the following descriptions of exemplary embodiments that are given for illustration of the invention and are not intended to be limiting thereof.

EXAMPLES

Example 1

An aqueous solution of Arg34-GLP-1[7-37] containing approximately 2% by weight ethanol and 10 mM of tris(hydroxymethyl)aminomethane, at pH 9.2 was made at room temperature, pH was adjusted to 3.2. The room temperature stability of the solution was monitored by RP-HPLC.

The solution was loaded on an ion-exchange column, Source 30S, Amersham Bioscience, at pH 3.23 and after washing the column with an acid buffer containing ethanol and citric acid, the product was eluted with an aqueous solution containing 10 mM Tris at pH 9.2. The room temperature stability of the eluate from the column was monitored by RP-HPLC (Table 1)/(FIG. 1).

TABLE 1

| Day | Arg34-GLP-1[7-37] concentration in loading solution | Arg34-GLP-1[7-37] eluate concentration |
| --- | --- | --- |
| 0 | 1.7 mg/ml | 1.4 mg/ml |
| 1 | 1.7 mg/ml | 1.4 mg/ml |
| 2 | 1.7 mg/ml | 1.4 mg/ml |
| 3 | Not analyzed | 1.3 mg/ml |

TABLE 1-continued

| Day | Arg34-GLP-1[7-37] concentration in loading solution | Arg34-GLP-1[7-37] eluate concentration |
| --- | --- | --- |
| 4 | Not analyzed | Not analyzed |
| 5 | 1.7 mg/ml | Not analyzed |

Gelation/fibrillation/aggregation was not observed in either of the samples tested.

Comparative Example 1

A comparative test with 20-200 mM glycine instead of tris(hydroxymethyl)aminomethane was done.

An aqueous solution of Arg34-GLP-1[7-37] containing approximately 2% by weight ethanol and 20 mM of glycine, at pH 9.0 was made at room temperature, pH was adjusted to approximately 3.3.

The solution was loaded to an ion-exchange column, Source 30S, Amersham Bioscience, at pH 3.3 and after wash of the column with an acid buffer containing ethanol and citric acid, the product was eluted with an aqueous solution containing 200 mM Glycine at pH 9.5. The stability of the eluate from the column was monitored by RP-HPLC at room temperature for 5 days.

Both loading solution and the eluate exhibited stability of less than one day at room temperature as a result of fibrillation.

Example 2

An aqueous solution of Arg34-GLP-1[7-37] containing approximately 2% by weight ethanol and 10 mM of tris (hydroxymethyl)aminomethane, at pH 9.2 was made at room temperature by dissolution of an Arg34-GLP-1[7-37] isoelectric precipitate directly in the solution. Subsequently, pH was adjusted to 3.2.

A preparative aliquot of the solution was loaded on a large scale ion-exchange column, 20 cm I.D. (internal diameter), Source 30S, Amersham Bioscience, at pH 3.3 and after washing the column with an acid buffer containing ethanol and citric acid to remove impurities, the product was eluted with an aqueous solution containing 10 mM Tris at pH 9.2. The column was regenerated with 1 M NaOH, equilibrated with the acidic wash buffer, and the column was loaded again with loading solution. Eluate from the Source 30S column was automatically pH adjusted with 100 mM tris buffer pH 7.4 to pH 8.0.

After 60 runs on the Source 30S column no change in pressure was observed, thus no fibrillation had occurred on the column, and no fibrillation was observed in loading solution and eluate.

Example 3

An aqueous solution of $N^\epsilon$-hexadecanoyl-γ-glutamyl-Lys26-Arg34-GLP-1[7-37] containing approximately 2% by weight ethanol and 10 mM of tris(hydroxymethyl)aminomethane, at pH 9.2 was made at room temperature by dissolution of an $N^\epsilon$-hexadecanoyl-γ-glutamyl-Lys26-Arg34-GLP-1[7-37] isoelectric precipitate directly in the solution.

A preparative aliquot of the solution was loaded on a large scale ion-exchange column, 45 cm I.D. (internal diameter), Source 30Q, Amersham Bioscience, at pH 9.2 and after washing the column with an buffer containing 20 mM tris and 63% by weight ethanol (pH 7.5) to remove impurities, the product was eluted by a sodium chloride gradient at pH 7.5 in a 20 mM tris buffer containing 63% by weight ethanol. The column was regenerated with 1 M NaOH, equilibrated with the pH 7.5 wash buffer, and the column was loaded again with loading solution. Eluate from the Source 30Q column was automatically diluted with water before it was loaded on another large scale column, RP-HPLC column 100 Å C-18, particle diameter 15 μm, column I.D. 45 cm, and eluted with a buffer solution containing 20 mM tris, 125 mM sodium chloride and approx. 45% by weight ethanol at pH 6.9. The column was regenerated with a 70% ethanol solution and subsequently equilibrated with a 25% ethanol solution containing 20 mM Tris.

After 60 runs on both the Source 30Q column as well as the RP-HPLC column no change in pressure was observed, thus no fibrillation had occurred on the column, and no fibrillation was observed in loading solutions and eluates.

Example 4

An aqueous solution of Arg34-GLP-1[7-37] containing approximately 2% by weight ethanol and 10 mM of tris (hydroxymethyl)aminomethane, at pH 9.2 was made at room temperature, pH was adjusted to 3.2.

Aliquot of the solution was loaded to an ion-exchange column, 45 cm i.d., Source 30S, Amersham Bioscience, at pH 3.3 and after wash of the column with an acid buffer containing ethanol and citric acid, the product was eluted with an aqueous solution containing 10 mM Tris at pH 9.2. The column was regenerated and loaded again with loading solution.

After 283 runs on the Source 30S column, without change in pressure, the column material was analyzed for aggregated/fibrillated proteins and there was no observation of proteins or aggregated/fibrillated proteins on the column material.

Example 5

An aqueous solution of $N^\epsilon$-hexadecanoyl-γ-glutamyl-Lys26-Arg34-GLP-1[7-37] containing approximately 2% by weight ethanol and 10 mM of tris(hydroxymethyl)aminomethane, at pH 9.2 was made at room temperature. Aliquot of the solution was loaded to an ion-exchange column, 45 cm i.d., Source 30Q, Amersham Bioscience, at pH 9.2 and after wash of the column with an neutral buffer containing 20 mM tris and 63% by weight ethanol (pH 7.5), the product was eluted by an sodium chloride gradient at pH 7.5 in a 20 mM tris buffer containing 63% by weight ethanol. The column was regenerated and loaded again with loading solution. One eluate from the Source 30Q column was automatically diluted with water before it was applied to an other column, RP-HPLC column 100 Å C-18, particle diameter i.d. 15 μm, column i.d. 45 cm, and eluted with a buffer containing 20 mM tris, 125 mM sodium chloride and approx. 45% by weight ethanol at pH 6.9.

After 77 runs on the Source 30Q column, without change in pressure, the column material was analyzed for aggregated/fibrillated proteins and there was no observation of aggregated/fibrillated proteins on the column material.

The RP-HPLC column material was analyzed after 49 runs for aggregated/fibrillated proteins and again there were no observations of aggregated/fibrillated proteins on the column material.

The results of the experiments show that processing and purification can be stabilized by the use of TRIS, both as an additive and as a buffer substance.

All references, including publications, patent applications, and patents, cited herein are hereby incorporated by reference to the same extent as if each reference were individually and specifically indicated to be incorporated by reference and were set forth in its entirety herein (to the maximum extent permitted by law).

Any combination of the above-described elements in all possible variations thereof is encompassed by the invention unless otherwise indicated herein or otherwise clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted and should be read as encompassing the phrases "consisting", "substantially comprised of," and "consisting essentially of" (e.g., where a disclosure of a composition "comprising" a particular ingredient is made, it should be understood that the invention also provides an otherwise identical composition characterized by, in relevant part, consisting essentially of the ingredient and (independently) a composition consisting solely of the ingredient).

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

What is claimed is:

1. A method for reducing gelation/fibrillation/aggregation of peptides, polypeptides and proteins during up-/downstream processing and purification, comprising the sequential steps:

(a) adding an amount of tris(hydroxymethyl)aminomethane to an aqueous solution of peptide, polypeptide or protein sufficient to induce stabilization of the peptide, polypeptide or protein, wherein the tris(hydroxymethyl)-aminomethane is a buffering agent or an additive and wherein the aqueous solution further comprises an organic modifier which is selected from: methanol, ethanol, 1-propanol, 2-propanol, butanol, hexylene glycol, acetonitrile, and N-methyl-2-pyrrolidone; wherein the organic modifier is present in a concentration from about 1% w/w to about 70% w/w;

(b) fractionating the aqueous solution of (a) by ion-exchange chromatography; and (c) fractioning the aqueous solution of (b) by reversed phase high performance liquid chromatography, or (b) fractionating the aqueous solution of (a) by reversed phase high performance liquid chromatography; and (c) fractioning the aqueous solution of (b) by ion-exchange chromatography, wherein the fractionating the aqueous solution by ion-exchange chromatography and fractioning the aqueous solution by reversed phase high performance liquid chromatography steps are performed without increasing back pressure on a chromatographic column, wherein gelation/fibrillation/aggregation of peptides, polypeptides and proteins during up-/down-stream processing and purification is reduced.

2. The method according to claim 1, wherein the organic modifier is present in a concentration from about 1% w/w to about 50% w/w.

3. The method according to claim 1, wherein the aqueous solution has a tris(hydroxymethyl)aminomethane concentration of from about 1 mM to about 1000 mM.

4. The method according to claim 3, wherein the aqueous solution has a tris(hydroxymethyl)aminomethane concentration of from about 1 mM to about 200 mM.

5. The method according to claim 3, wherein the aqueous solution has a tris(hydroxymethyl)aminomethane concentration of from about 1 mM to about 100 mM.

6. The method according to claim 3, wherein the aqueous solution has a tris(hydroxymethyl)aminomethane concentration of from about 2 mM to about 75 mM.

7. The method according to claim 3, wherein the aqueous solution has a tris(hydroxymethyl)aminomethane concentration of from about 3 mM to about 50 mM.

8. The method according to claim 3, wherein the aqueous solution has a tris(hydroxymethyl)aminomethane concentration of from about 5 mM to about 25 mM.

9. The method according to claim 1 wherein the aqueous solution has a pH from about 1.0 to about 10.0.

10. The method of claim 9 wherein the aqueous solution has a pH from about 2.0 to about 10.0.

11. The method of claim 9 wherein the aqueous solution has a pH from about 3.0 to about 9.5.

12. The method according to claim 1, wherein the peptide, polypeptide or protein is selected from: Glucagon-Like Peptides (GLPs) and analogs and derivatives thereof.

13. The method according to claim 12, wherein the GLPs is selected from the group: GLP-1 and GLP-1 analogs and derivatives thereof, GLP-2 and GLP-2 analogs and derivatives thereof, and exendin-4 and analogs and derivatives thereof.

14. The method according to claim 12, wherein the Glucagon-Like Peptide (GLP) is GLP-1, and analogs and derivatives thereof.

15. The method according to claim 12, wherein the Glucagon-Like Peptide (GLP) is GLP-2, and analogs and derivatives thereof.

16. The method according to claim 12, wherein the Glucagon-Like Peptide (GLP) is exendin-4, and analogs and derivatives thereof.

17. The method according to claim 1, wherein the peptide, polypeptide or protein is selected from: proinsulins, insulins, and analogs and derivatives thereof.

18. The method according to claim 17, wherein the peptide, polypeptide or protein is insulin and analogs and derivatives thereof.

* * * * *

UNITED STATES PATENT AND TRADEMARK OFFICE
CERTIFICATE OF CORRECTION

| | | |
|---|---|---|
| PATENT NO. | : 8,710,181 B2 | Page 1 of 1 |
| APPLICATION NO. | : 11/661521 | |
| DATED | : April 29, 2014 | |
| INVENTOR(S) | : Christainsen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1051 days.

Signed and Sealed this
Eleventh Day of August, 2015

Michelle K. Lee
*Director of the United States Patent and Trademark Office*